United States Patent
Emmerich et al.

(10) Patent No.: US 9,539,160 B2
(45) Date of Patent: Jan. 10, 2017

(54) MEDICAL APPLIANCE, AND MEDICAL APPLIANCE SYSTEM

(71) Applicant: Karl Storz GmbH & Co. KG, Tuttlingen (DE)

(72) Inventors: Bernd Emmerich, Engen (DE); Andreas Jansche, Zimmern ob Rottweil (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 14/085,160

(22) Filed: Nov. 20, 2013

(65) Prior Publication Data
US 2014/0138331 A1    May 22, 2014

(30) Foreign Application Priority Data
Nov. 22, 2012 (DE) .................... 10 2012 111 260

(51) Int. Cl.
*A61G 12/00*    (2006.01)

(52) U.S. Cl.
CPC .............. *A61G 12/00* (2013.01); *A61B 50/13* (2016.02); *A61B 90/00* (2016.02); *A61G 12/002* (2013.01); *A61G 12/004* (2013.01); *A61G 12/005* (2013.01); *A61G 12/008* (2013.01)

(58) Field of Classification Search
CPC .... A61G 12/002; A61G 12/00; A61G 12/008; A61G 12/004; A61G 12/005; A61G 13/107; A61B 2019/025; A61B 19/26; A61B 19/0248; A47B 57/12; H01R 13/6215; H01R 2201/12

USPC ...... 312/209, 351; 211/85.13; 439/532, 543, 439/551, 362

See application file for complete search history.

(56) References Cited

U.S. PATENT DOCUMENTS

| | | | | | |
|---|---|---|---|---|---|
| 625,271 | A | * | 5/1899 | Lang | 211/85.13 |
| 2,788,902 | A | * | 4/1957 | Nowicki | 108/157.13 |
| 3,761,968 | A | * | 10/1973 | Besler | 5/503.1 |
| 4,066,318 | A | * | 1/1978 | Vonder et al. | 439/362 |
| 4,285,559 | A | * | 8/1981 | Koch | 312/298 |
| 4,429,938 | A | * | 2/1984 | Flor | H01R 13/625 403/349 |
| 4,489,995 | A | * | 12/1984 | Barr | 312/236 |
| 4,565,395 | A | * | 1/1986 | Rockwood | F16B 7/1427 248/415 |
| 4,600,251 | A | * | 7/1986 | Zimmerman | 312/209 |
| 4,674,722 | A | * | 6/1987 | Danby | A61M 5/1415 24/134 KB |

(Continued)

FOREIGN PATENT DOCUMENTS

| | | |
|---|---|---|
| DE | 2348686 A1 | 4/1975 |
| DE | 8631635 U1 | 1/1987 |

(Continued)

*Primary Examiner* — Joshua Rodden
*Assistant Examiner* — Hiwot Tefera
(74) *Attorney, Agent, or Firm* — Whitmayer IP Group LLC (57) ABSTRACT

A medical appliance for use in a medical environment has a holding mechanism for holding the appliance on a support device assigned to the medical environment, and an attachment mechanism for attaching the appliance to at least one electrical connection line, wherein the holding mechanism is designed as at least one support bolt connected to a support structure of the appliance, and wherein the support bolt has the attachment mechanism. The invention also relates to a medical appliance system.

16 Claims, 6 Drawing Sheets

(56) References Cited

U.S. PATENT DOCUMENTS

| | | | | |
|---|---|---|---|---|
| 5,061,018 A | * | 10/1991 | Pederson et al. | 312/209 |
| 5,281,020 A | * | 1/1994 | Romick | 312/308 |
| 5,359,497 A | * | 10/1994 | Booth | 361/807 |
| 5,417,400 A | * | 5/1995 | Arakawa | 248/323 |
| 5,513,827 A | * | 5/1996 | Michelson | A61B 17/02 |
| | | | | 248/160 |
| 5,563,457 A | * | 10/1996 | Booth | 307/106 |
| 5,695,261 A | * | 12/1997 | Slesinger et al. | 312/223.6 |
| 5,890,929 A | * | 4/1999 | Mills | H01R 13/6599 |
| | | | | 439/607.03 |
| 6,120,313 A | * | 9/2000 | Luich et al. | 439/362 |
| 6,153,864 A | * | 11/2000 | Hammen | H05B 6/103 |
| | | | | 156/380.2 |
| 6,196,649 B1 | * | 3/2001 | Block et al. | 312/209 |
| 6,591,996 B1 | * | 7/2003 | Wu | 211/90.02 |
| 7,001,126 B2 | * | 2/2006 | Lesecq | 411/340 |
| 7,081,024 B2 | * | 7/2006 | Karadimas et al. | 439/680 |
| 7,221,123 B2 | * | 5/2007 | Chen | B60L 11/1822 |
| | | | | 280/28.12 |
| 7,401,810 B2 | * | 7/2008 | Brisighella, Jr. | B60R 21/26 |
| | | | | 280/736 |
| 7,520,288 B2 | * | 4/2009 | Rhodes | B08B 3/02 |
| | | | | 134/200 |
| 7,645,142 B2 | * | 1/2010 | McMunigal et al. | 439/6 |
| 7,708,586 B1 | | 5/2010 | Rohde et al. | |
| 7,884,735 B2 | * | 2/2011 | Newkirk | A61G 7/012 |
| | | | | 211/26 |
| 8,037,833 B2 | * | 10/2011 | Hardy | 108/91 |
| 8,191,489 B1 | * | 6/2012 | Smith | 108/186 |
| 9,089,066 B2 | * | 7/2015 | Kajackas | A61G 12/00 |
| 2003/0037375 A1 | | 2/2003 | Riley et al. | |
| 2006/0242763 A1 | * | 11/2006 | Graham | A61G 7/0503 |
| | | | | 5/503.1 |
| 2007/0125738 A1 | * | 6/2007 | Sevack | 211/187 |
| 2009/0020656 A1 | * | 1/2009 | Cave | 248/74.2 |
| 2009/0026901 A1 | * | 1/2009 | Nies et al. | 312/249.11 |
| 2009/0197460 A1 | * | 8/2009 | Kent | H01R 13/508 |
| | | | | 439/518 |
| 2010/0072328 A1 | * | 3/2010 | Burnham et al. | 248/49 |
| 2012/0103925 A1 | * | 5/2012 | Kitt et al. | 211/134 |
| 2012/0203377 A1 | | 8/2012 | Paydar et al. | |
| 2014/0321096 A1 | * | 10/2014 | Kajackas | 361/807 |

FOREIGN PATENT DOCUMENTS

| | | |
|---|---|---|
| DE | 4210433 A1 | 10/1993 |
| DE | 19859473 B4 | 4/2005 |
| DE | 112004000387 T5 | 3/2006 |
| DE | 69935622 T2 | 12/2007 |
| DE | 102009024335 A1 | 12/2010 |
| DE | 202011108124 U1 | 2/2013 |
| EP | 2058911 A1 | 5/2009 |
| WO | 9936024 A1 | 7/1999 |
| WO | 2011004154 A1 | 1/2011 |
| WO | 2013102494 A1 | 7/2013 |

* cited by examiner

MEDICAL APPLIANCE, AND MEDICAL APPLIANCE SYSTEM

FIELD OF THE INVENTION

The invention relates to a medical appliance for use in a medical environment, comprising holding means for holding the appliance on a support device assigned to the medical environment, and attachment means for attaching the appliance to at least one electrical connection line. The invention further relates to a medical appliance system, which comprises a plurality of such medical appliances and also a support device for the plurality of medical appliances.

BACKGROUND OF THE INVENTION

In the medical field, particularly in surgical operations, or also in intensive care medicine, various kinds of electrical and electronic medical appliances are often needed, for example in order to supply energy to endoscopes or surgical instruments and to control them, and also in order to monitor vital functions of a patient. Such appliances should be able to be arranged close to the patient in a way that takes up as little space as possible, without impeding access to the patient, and they should also be able to be fitted in place, connected and operated easily and safely and, if appropriate, should be able to be quickly exchanged.

It is known to install medical appliances of this kind on a carriage, for example, on stationary operating theater furniture, or also on one or more consoles held on a pivotable ceiling arm fastened to the ceiling of an operating theater. In these cases, however, the appliances are not sufficiently secured against falling or against unauthorized removal. The consoles themselves, which are needed to install the appliances, take up a considerable amount of space and increase the overall weight of the arrangement. The electrical attachments for mains voltage and data lines are arranged freely accessibly, and the corresponding lines have to be attached individually to the respectively corresponding attachments. For plugging and unplugging electrical lines or light-guiding cables, and in further maneuvers, two hands are often needed, in order to be able to apply the necessary opposing force and to avoid undesired movement of the appliance. The freely accessible lines and the large overall surface area of the appliance housings cause increased cleaning work.

EP 2 058 911 A1 discloses a medical supply unit for supplying power and transferring data in medical apparatus, which supply unit comprises an elongate carrier, with a coupling device that extends along the carrier and that has at least two continuous, electrically insulated conductor rails. The coupling device is designed as a hollow rail, with the conductor rails arranged on the inner face thereof. A modular component has a coupling piece, which produces the contact with the conductor rails. Replacement of an individual medical appliance is not easily possible here. Moreover, the weight that can be taken up by the coupling device, and the number and nature of the connections that can be produced in this way for power supply and data transfer, are relatively limited.

According to DE 699 35 622 T2, an attachment plate for receiving an instrument comprises a plate, a rail mounted on the plate at a distance from the plate, and a signal port secured in the plate, which signal port can be coupled to an electrical port of the housing of the instrument. Here too, the weight of the instruments that can be taken up is very limited. Moreover, the instruments on the attachment plate are not sufficiently secured against falling or against unauthorized removal.

SUMMARY OF THE INVENTION

The object of the present invention is to specify a medical appliance of the type in question, and a medical appliance system, free of the abovementioned disadvantages.

This object is achieved by the claimed medical appliance. Advantageous developments of the invention are set forth in the dependent claims.

A medical appliance according to the invention is designed for use in a medical environment, particularly in an operating theater of a hospital or day clinic, but also for example in a preparation area or examination area of a medical practice. An appliance of this kind is in particular a supply or control appliance for a surgical instrument or an endoscope, for example an HF generator, a light source, or an irrigation or insufflation pump. However, the appliance can also be, for example, a monitor for vital parameters of the patient, or a control part of a central operating theater control system.

The medical appliance has holding means for mechanically holding the appliance on a support device assigned to the medical environment. The support device can be a movable carriage for appliances, a ceiling supply arm fastened to a room ceiling, or a stationary item of operating theater furniture, or it can be arranged on a movable carriage, on a ceiling arm, on an item of operating theater furniture, or also on a wall of an operating theater, or can be integrated therein. The support device can in particular comprise a fastening means which is designed in the shape of a plate or rail and which interacts with the holding means of the appliance to hold the appliance.

The medical appliance also has attachment means for attaching the appliance to at least one electrical connection line. The electrical connection line can serve to supply power to the appliance and/or to transfer data, and it can have a single-core or multi-core design. The electrical connection line can be part of the support device or can be routed independently of the latter. Preferably, the electrical connection line is assigned to the medical environment and serves, for example, to connect the appliance to a voltage supply and to a central operating theater control system.

According to the invention, the holding means are designed as at least one support bolt connected to a support structure of the appliance. The support structure of the appliance can be, for example, a frame of the appliance or also a self-supporting housing of the appliance. The support bolt preferably protrudes from the support structure or from the appliance, in order to make it easier to fit the appliance on the support device. The appliance can have a substantially closed housing, in which case the support bolt juts out from a wall of the housing, in particular from a rear wall or side wall of the housing. The support bolt can be designed to be releasably connectable to the support structure and may have been connected to the support structure of the appliance at the time of an assembly or configuration of the appliance.

According to the invention, the support bolt has the attachment means for attaching the appliance to the at least one electrical connection line. In addition, further attachment means, for example for attachment of a fiber-optic line or a gas line or liquid line, may be present, which can comprise corresponding optical components or sealing elements and which are preferably likewise enclosed by the at least one support bolt. For connection to a functional element powered or controlled by the medical appliance, for example to a sensor, a surgical instrument or an endoscope, further attachment means can also be provided which are not enclosed by the support bolt and which are preferably arranged on a front face of the appliance or of the housing and are therefore particularly easy to access by a user.

According to the invention, a medical appliance is thus made available in which both the mechanical holding of the appliance and also the production of an electrical connection in a medical environment are simplified. In this way, the medical appliance can be quickly fitted and secured against falling and provided with the electrical connections needed for its operation. By virtue of the fact that the holding means are designed as at least one support bolt connected to the support structure of the appliance, mechanical holding of the appliance is permitted by the at least one support bolt alone, and fitting the appliance on the support device is made easier in this way. By virtue of the fact that the appliance is held firmly on the support device, two hands are no longer necessarily required when inserting and removing plugs. Moreover, by virtue of the fact that the support bolt has the attachment means for attaching the appliance to the at least one electrical connection line, attaching the appliance to the connection line is made easier. Insofar as the medical appliance has a housing, this also means that the number of necessary gaps in the housing is reduced, which is advantageous for reasons of hygiene in a medical environment.

Preferably, the medical appliance has only a single support bolt of this kind, which is designed to hold the appliance on the support device and which comprises all the necessary attachment means for attaching the appliance to the at least one electrical connection line. The mechanical connection and the electrical connection can thus be produced jointly via a suitably stable support bolt as the single mechanical/electrical coupling means. This further simplifies both the mechanical fitting and also the production of the electrical connections needed for operating the appliance. Moreover, since the number of handling steps for mechanical fitting and electrical connection and the number of areas of the appliance to be handled for this purpose are reduced, the number of possible errors is reduced; since each handling step may also be associated with a contamination of the appliance, this also reduces the hygiene risk and makes cleaning easier. Particularly in appliances with a high inherent weight, however, it is also possible for more support bolts to be provided.

According to a preferred embodiment of the invention, the attachment means are designed as plug contacts arranged on an end face of the support bolt directed away from the appliance. The plug contacts can be contact pins for example, which can engage in one or more sockets of the connection line. However, the plug contacts can also form sockets for example, which are provided for receiving contact pins assigned to the connection line. It is also possible for the support bolt to have both contact pins and also socket-like plug contacts, which are designed to cooperate with complementary sockets or contact pins of the connection line. Advantageously, the plug contacts of the support bolt are oriented in a longitudinal direction of the support bolt, such that corresponding plug contacts of the connection line are able to be pushed on in the longitudinal direction of the support bolt. It is particularly preferable that the plug contacts of the support bolt are arranged for cooperation with a single plug of the connection line, which plug has corresponding contact pins and/or sockets and can be pushed onto the support bolt in the longitudinal direction thereof. In this way, attaching the appliance to the electrical connection line is also made easier.

It is also preferable that the support bolt has an outer thread at least in some parts. The outer thread makes it possible, for example, for a nut to be screwed on and secured on the support device. The outer thread can also serve to fasten the support bolt on the support structure of the appliance. By this means, the support bolt can be reliably and firmly fixed on the appliance and on the support device in a simple way.

According to a preferred embodiment of the invention, the support structure of the appliance has an oblong hole. The oblong hole can be designed, for example, as a slit of a housing, in particular as a slit of a self-supporting housing; particularly in a customary set-up of the appliance, the slit is a horizontal longitudinal slit of the housing. The support bolt is movable in the oblong hole and can be fixed in a plurality of positions, preferably in any desired positions, on the support structure. This allows the appliance to be positioned in a desired position relative to the support device, particularly in a horizontal direction, and to be fixed in this position.

The support bolt, in the area thereof near the appliance, advantageously has at least two, preferably exactly two, first flat surfaces lying opposite each other in a pair, which cooperate with the oblong hole in such a way that the support bolt is movable inside the oblong hole and is guided in a manner secure against twisting. The first flat surfaces extend, at least along part of the length of the support bolt, parallel to the longitudinal axis thereof. In the non-flattened areas, the support bolt can have an outer thread, with which the support bolt, for example with the aid of a nut and a mating nut, can be screwed at a plurality of positions in the oblong hole. The support bolt is preferably steplessly adjustable. By this means, the appliance can be easily fastened to the support device in a way that is adaptable to specific spatial requirements.

It is also preferable that the support bolt, in its area directed away from the appliance, has at least two second flat surfaces lying opposite each other, which can extend in the longitudinal direction of the support bolt as far as the end thereof away from the appliance. Preferably, the support bolt has exactly two second flat surfaces lying opposite each other. Thus, in a similar way to that described above, it is able to move in a corresponding oblong hole or slit of the support device. The non-flattened areas can have an outer thread, such that the support bolt can be fastened, for example using a nut and a mating nut, on a fastening plate of the support device provided with such an oblong hole. This permits fixing in a plurality of positions, preferably at any desired position in the oblong hole, as a result of which the appliance can be mounted and fixed in a particularly simple way at different positions on the support device.

Particularly preferably, two first and two second flat surfaces are provided, in which case the first and second flat surfaces are mutually offset by ca. 90° with respect to a longitudinal axis of the support bolt. It is thus possible for the appliance, of which the support structure has an oblong hole extending in a first direction, to be fastened in a large number of possible positions on a support device that has an oblong hole extending in a second direction substantially perpendicular to the first direction. In particular, the first direction can be oriented horizontally and the second direction vertically, such that the appliance can be fixed at any desired height on a fastening plate with a vertical oblong hole and can be moved along the oblong hole of the appliance to a desired horizontal position.

An appliance system according to the invention comprises at least two medical appliances, which are designed as described above, and a support device for the appliances. The medical appliances can in particular be part of a modular system and, by their combination and configuration, can be adapted to different requirements, for example to different operating areas. The support device has a fastening plate provided with at least one aperture, wherein the support bolts of the medical appliances are designed for inserting into the aperture and for fastening on an area of the fastening plate adjacent to the aperture, such that the medical appliances can be held on the fastening plate. The fastening plate can also be designed as a fastening rail, for example. In particular, the support bolt is in each case designed in such a way that its end area directed away from the appliance can be guided through the aperture and can be fixed on the fastening plate of the support device by a fastening means engaging behind the aperture. Alternatively, the support bolt can be designed in such a way that its end area directed away from the appliance can be guided into the aperture and is held with a force fit or form fit in the aperture, without a fastening means engaging behind the aperture, in which case a blind hole can be provided instead of the aperture, and the support device can, for example, be part of a wall of a room.

The support device can, for example, be a movable carriage, an item of operating theater furniture, or a ceiling arm mounted on a ceiling of an operating theater, or it can be fastened on such a carriage, on an item of operating theater furniture, or on a ceiling arm, or also on a wall of the medical environment, or can be integrated therewith. The support device can comprise the at least one electrical connection line of a respective appliance, or the connection line can be routed separately from the support device. Preferably, the respective electrical connection line has a plug which cooperates with the attachment means, assigned to the attachment bolt, to produce all the electrical connections needed for operating the appliance. The connection line can be assigned to the medical environment and, for example, can serve for voltage supply to the appliance in question and for data exchange with a central operating theater control system. The connection line can also be assigned to the support device and, for example, can be connected to a supply line and data line of the medical environment. The connection line can also serve to connect an appliance to one or more further appliances.

The appliance system according to the invention provides a simple and reliable way of fastening the medical appliances in a manner adapted to the particular requirement and of at the same time creating the necessary electrical connections.

Preferably, the aperture of the fastening plate of the support device is a hole in a grid-like pattern of holes or is an oblong hole. By arranging the apertures in the form of a grid-like pattern of holes, it is possible to ensure a fixed arrangement of horizontally or vertically stacked appliances, which have standardized dimensions, and thus ensure particularly simple and exact fitting on the support device. An oblong hole permits a stepless adaptation of the fastening position of the appliance to different requirements, in particular to different heights of the appliances with which it can form a stack. In particular, an oblong hole in the fastening plate can be oriented in the vertical direction, in order to permit an arrangement of appliances at different heights and, for example, to allow appliances of different heights to be stacked in the vertical direction.

Preferably, the medical appliance system has a nut which can be screwed onto an area of the support bolt that can be guided through the aperture, in particular onto an outer thread of the support bolt, from the direction of the end facing away from the appliance. To further improve the fixing, the nut can be provided with a flange and/or a washer can be provided, wherein the flange or the washer engages behind the aperture. Particularly preferably, the nut is at the same time designed to secure a plug of the connection line, which plug can be fitted onto plug contacts arranged on the end face of the support bolt directed away from the appliance. In this way, in a single working step, it is possible to obtain both a secure mechanical fixing on the support device and also a secured electrical connection to the at least one connection line. The nut and the washer can be part of the medical appliance system.

According to a preferred embodiment of the invention, the medical appliances of the medical appliance system are designed such that they are able to be stacked, wherein a top face and a bottom face of the appliance are shaped in such a way that the bottom face of a first appliance can be placed with a form fit onto the top face of a second appliance. The appliance can be able to be stacked horizontally or vertically for example, the terms "top face" and "bottom face" relating to the direction of stacking. Thus, for example, appliances of this kind can be stacked vertically on a horizontal console or on a carriage, while such appliances can be able to be stacked, suspended on a ceiling supply device, in the vertical or horizontal direction. By this means, the appliances can be safely arranged in a way that saves space.

It is also preferable that the appliance has a substantially fully closed housing and, on a lower edge of a front face of the housing, carries a protruding lip. The protruding lip of a first appliance overlaps the upper edge of a front face of the housing of a second appliance arranged underneath in a vertical stack, such that entry of liquids between the appliances is avoided. Such liquids may be, for example, blood or irrigation liquid which, as a result of leaks, or upon fitting or removal of corresponding hoses of a pump, can settle on the front face of an appliance designed as a pump. By virtue of the fact that the appliances overlap each other like roof tiles, at least on their front face, cleaning the appliances is made easier.

According to a preferred embodiment of the invention, the housing of the first and second appliances in each case has a rear wall and/or a side wall, wherein the support bolt of the respective appliance protrudes from the rear wall or side wall. The appliances can thus be mounted and fixed on a fastening plate, for example a fastening rail, which is arranged on the rear or side of the appliances. This permits secure mechanical retention, and an electrical connection that does not impede the operability of control elements arranged on a front face of the respective housing. In particular, if the support bolts and the fastening plate are arranged at the side, this also provides particularly good access to the support bolts, as a result of which the mechanical fixing and the production of the electrical connection are further simplified.

A holding device for a medical appliance comprises at least one support bolt, for holding a medical appliance, and a support device, which are designed as described above, and, if appropriate, a nut and a washer for fixing the support bolt on the fastening plate of the support device. The holding device can also comprise means for fastening the support bolt on the medical appliance.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached schematic drawing, in which.

DETAILED DESCRIPTION OF THE INVENTION

Figure 1:
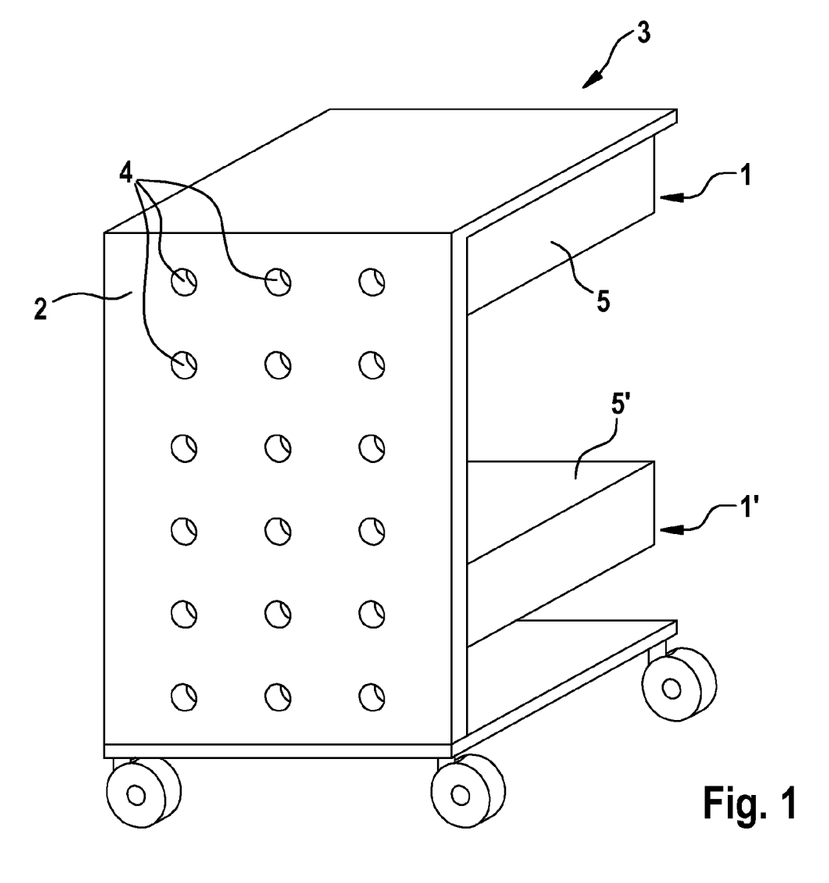
FIG. 1 shows a support device designed as a carriage with a fastening plate and with two medical appliances according to a first illustrative embodiment of the invention.

An example of a support device, with appliances 1, 1' held thereon, is shown in a simplified form in FIG. 1. The support device comprises a vertical fastening plate 2 and is designed as a carriage 3 that can be moved on rollers. The medical appliances 1, 1' are, for example, supply and control appliances for surgical instruments and/or endoscopes. The fastening plate 2 has a grid-like pattern of holes comprising circular through-holes 4. In the state shown by way of example in FIG. 1, two appliances 1, 1' are fastened on the fastening plate 2. For this purpose, at least one support bolt, which protrudes from a rear wall of the housing 5, 5' of the appliance 1, 1', is in each case inserted through at least one of the holes 4 and screwed (not shown in FIG. 1) onto the fastening plate 2. The dimensions of the appliances 1, 1', in particular the height, and the grid distances between the holes 4 are adapted to each other. As will be clear from the view in FIG. 1, a separate replacement of the appliances 1, 1', and of further appliances that can be fastened and attached at the remaining free positions under or between the appliances 1, 1', is easily possible for configuration work and servicing. In addition to the housings 5, 5', a surrounding housing (not shown) can be provided in order to additionally protect the appliances 1, 1' from contamination.

Figure 2:
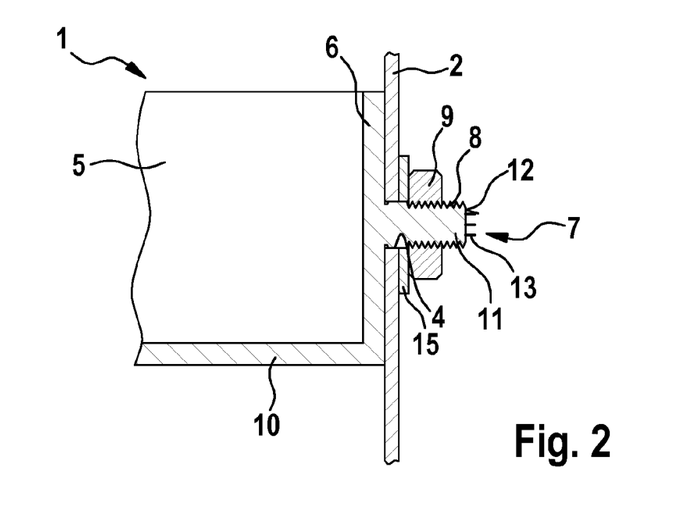
FIG. 2 shows a sectional view of a medical appliance and of a fastening plate according to the first illustrative embodiment.

As is shown schematically in a sectional view in FIG. 2, a support bolt 7 protrudes from a rear wall 6 of the housing 5 of the appliance 1 and is inserted into the hole 4 of the fastening plate 2. The support bolt 7 has an outer thread 8, onto which a nut 9 can be screwed. By tightening the nut 9 against the fastening plate 2, it is possible for the support bolt 7, and therefore the appliance 1, to be firmly fixed on the fastening plate 2, and, in order to improve the introduction of force into the fastening plate 2, a washer 15 can be arranged between the nut 9 and the fastening plate. The rear wall 6 of the housing 5 is strengthened to ensure secure holding of the appliance 1 and, as is indicated in FIG. 1, it forms, along with a bottom face 10 of the housing 5, a support structure of the appliance 1. The rear wall 6 and the bottom face 10 of the housing 5 are correspondingly stiffened, for example as a self-supporting chassis, in order to be able to take up the weight of the appliance 1 and also the forces that arise during use. The support bolt 7, like the fastening plate 2, is likewise designed to take up the necessary forces and can, for example, have a tubular bolt body 11 with corresponding wall thickness. The bolt body 11 can, for example, be formed integrally with the rear wall 6 of the housing 5 or can be screwed or welded onto said rear wall 6. As can likewise be seen from FIG. 2, the support bolt 7, on its end face 12 directed away from the appliance 1, carries a plurality of electrical contacts which, for example, are designed as contact pins 13 oriented in the axial direction of the support bolt 7. A plug of an electrical connection line (not shown in FIG. 2) with corresponding sockets can be fitted onto the contact pins 13. Electrical lines, connected to the contact pins 13, can be routed inside the support bolt 7 to corresponding contacts inside the appliance 1, or further contacts for connection to corresponding electrical lines (not shown in FIG. 2) inside the appliance can be arranged on the end face of the support bolt 7 directed toward the appliance.

Figure 3:
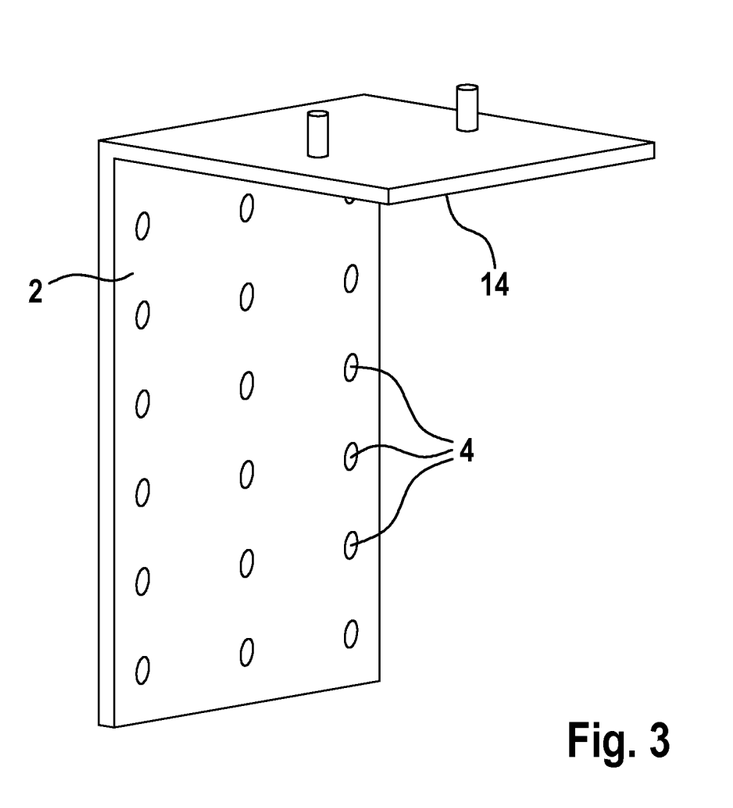
FIG. 3 shows a support device that can be fastened on a ceiling arm, with a fastening plate according to the first illustrative embodiment.

FIG. 3 shows an example of how a fastening plate 2, designed as in FIG. 1, is mounted on a ceiling holder 14 which, for example, can be mounted on a pivotable ceiling supply arm (see FIG. 5) arranged on a room ceiling or can also be mounted directly on a room ceiling.

Figure 4:
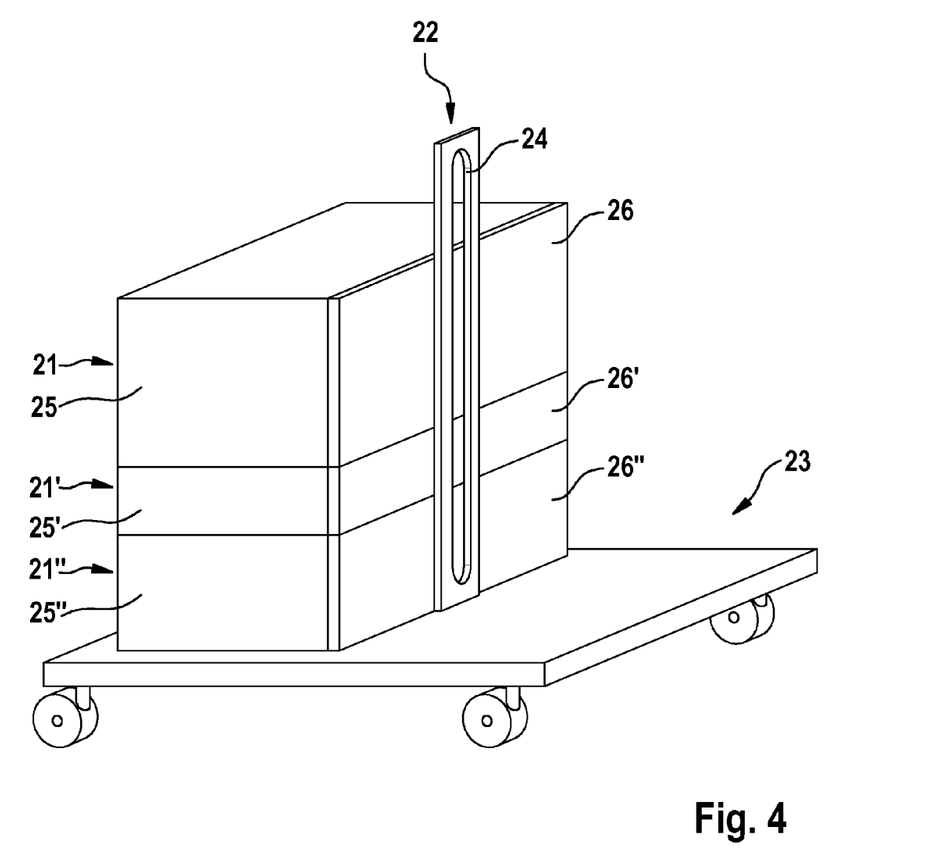
FIG. 4 shows a support device designed as a carriage with a fastening plate and with three medical appliances according to a second illustrative embodiment of the invention.

According to the further illustrative embodiment shown in FIG. 4, a medical appliance system according to the invention comprises a plurality of medical appliances 21, 21', 21" and a support device, which comprises a fastening plate 22, designed as a fastening rail, and which is designed as a movable carriage 23 provided with rollers. The fastening plate 22 is fastened vertically on a base plate of the carriage 23, for example by being screwed or welded thereon. The fastening plate 22 has an oblong hole 24 extending in the vertical direction. The appliances 21, 21', 21" are stacked on top of each other on the carriage 23. The appliances 21, 21', 21" each have a substantially fully closed housing 25, 25', 25". A top face of the housing 25', 25" of an appliance 21', 21" in each case establishes a form fit with a bottom face of the housing 25, 25' of the respective appliance 21, 21' stacked on top of it. To further secure the appliances 21, 21', 21" on the carriage 23, they lie with their rear wall 26, 26', 26" bearing on the fastening plate 22, and they can be fixed on the latter with the aid of a respective support bolt (see FIG. 7).

Figure 5:
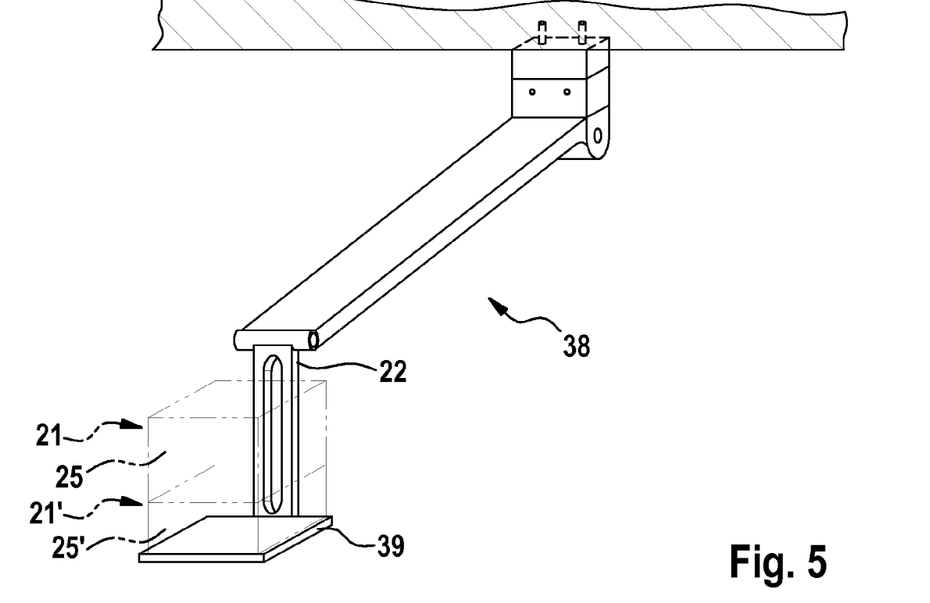
FIG. 5 shows a support device fastened on a ceiling arm, with a fastening plate according to the second illustrative embodiment.

As a further example of the arrangement of a fastening plate 22 designed as a fastening rail, FIG. 5 shows a pivotable ceiling arm 38 which is fastened to a room ceiling and on the lower end of which a fastening plate 22 is mounted on which appliances 25, 25' can be fixed as described above. To simplify the arrangement of the appliances 25, 25', a console 39 can be fastened on the lower end of the fastening plate 22. The fastening plate 2, 22 (see also FIG. 3) can also be arranged horizontally on the ceiling arm 38, such that the appliances 1, 1', 25, 25' are held suspended on the fastening plate 2, 22.

Figure 6:
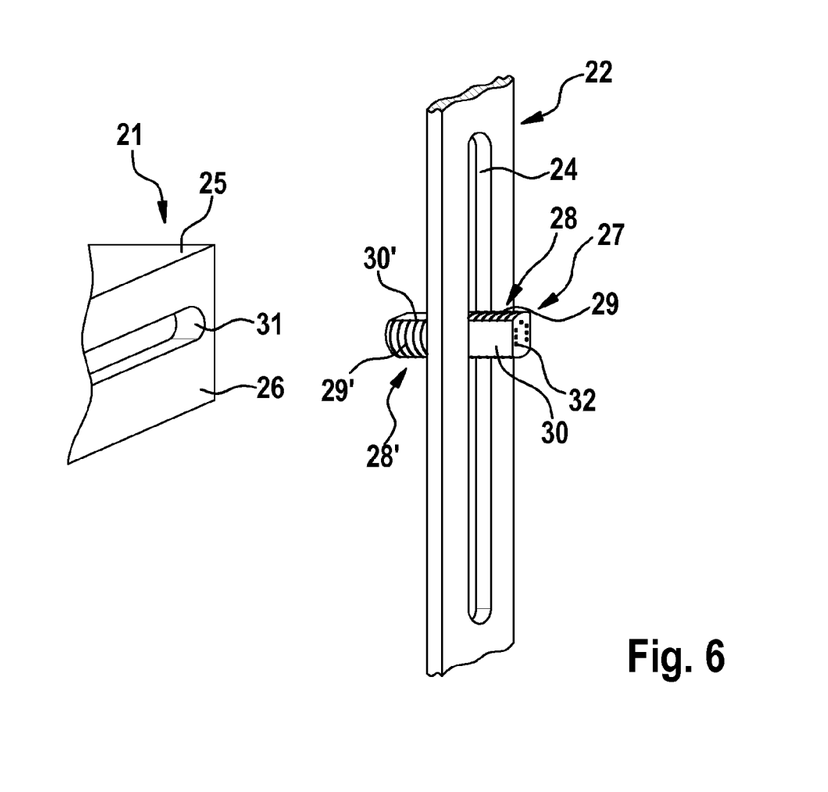
FIG. 6 shows a detail of a medical appliance and of a fastening plate according to the second illustrative embodiment.

FIG. 6 shows a support bolt 27, with which an appliance 21 can be fixed on the fastening plate 22 designed as a fastening rail. The support bolt 27 has a portion 28 directed away from the appliance and a portion 28' near the appliance. The portion 28 directed away from the appliance and the portion 28' near the appliance each have an outer thread 29, 29' in partial regions of their circumference lying opposite each other and, in the partial regions of their circumference lying therebetween, are provided with flat surfaces 30, 30'. In relation to a longitudinal axis of the support bolt 27, the flat surfaces 30' are offset by 90° with respect to the flat surfaces 30; the same applies for the area of the outer thread 29' with respect to the area of the outer thread 29.

As is shown schematically in FIG. 6, the support bolt 27 can be inserted, via its portion 28' near the appliance, into an oblong hole 31 of the rear wall 26 of the housing 25, which forms the support structure of the appliance 21. Here, the support bolt 27 can be connected to the appliance 21 by, for example, a nut which is screwed onto the outer thread 29' from the direction of the interior of the appliance; for mounting on the fastening plate, the support bolt 27 can remain movable (not shown) inside the oblong hole 31. To fix the appliance 21 on the fastening plate 22, the support bolt 27 is guided through the oblong hole 24 of the fastening plate 22 and can be held there by a nut that is screwed onto the outer thread 29. The flat surfaces 30, 30' permit an insertion of the support bolt 27 into the oblong hole 24, and likewise into the oblong hole 31, and a movement of the support bolt 27 in the oblong hole 24, 31 concerned, such that the appliance 21 can be placed in any desired position and, by tightening the nut fitted on the thread 29, can be fixed in this position. It may be sufficient that a nut is screwed onto the thread 29' on the inside face of the rear wall 26 and that a further nut is screwed onto the thread 29 of the support bolt 27 on that side of the fastening plate 22 directed away from the appliance 25. By tightening the latter nut, which is accessible from the outside, the appliance can be fixed securely on the fastening plate. The end face of the support bolt 27 directed away from the appliance has a plurality of contact sockets 32, into which corresponding contact pins of a plug (not shown in FIG. 5) can be fitted. Electrical lines, which are connected to the contact sockets 32, can be routed inside the support bolt 27 to corresponding contacts inside the appliance 25, or further contacts (not shown in FIG. 6) for connection to corresponding electrical lines inside the appliance can be arranged on the end face of the support bolt 27 directed toward the appliance. The support bolt 27 can be designed as an intermediate piece, separate from the appliance 25, for the mechanical retention and electrical attachment of the appliance 25.

Figure 7:
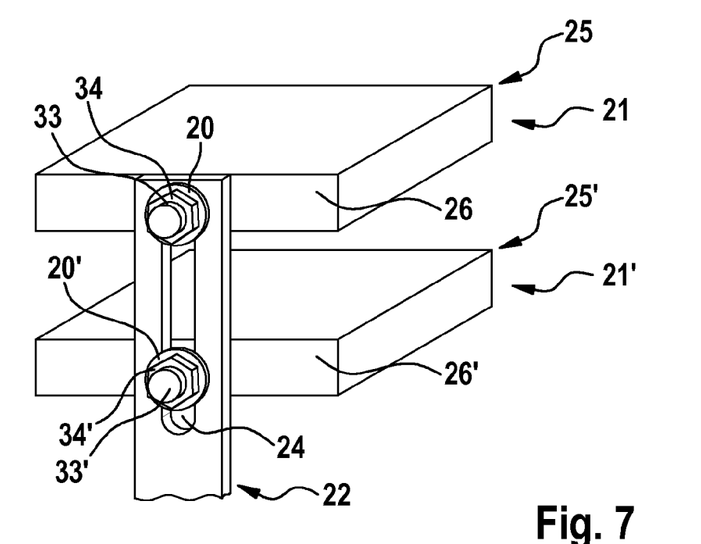
FIG. 7 shows a partial view of a fastening plate and of two medical appliances according to the second illustrative embodiment.

FIG. 7 shows an example of an arrangement of two medical appliances 25, 25', which are fixed on the fastening plate 22 by means of nuts 34, 34' being screwed onto the ends 33, 33' of the support bolts directed away from the appliance and being drawn tight via washers 20, 20' against the rear wall 26, 26', which is part of the support structure of the respective appliance 21, 21'. Moreover, in the illustrative embodiment shown in FIG. 7, a separate replacement of the appliances 21, 21', and of further appliances that can be fastened and attached at the remaining free positions between the appliances 21, 21', is easily possible. By fixing at a variable height inside the oblong hole 24, appliances of different height can be fixed easily and in a way that saves space. In addition to the housings 25, 25', a surrounding housing (not shown) can be provided in order to additionally protect the appliances 21, 21' from contamination.

Figure 8:
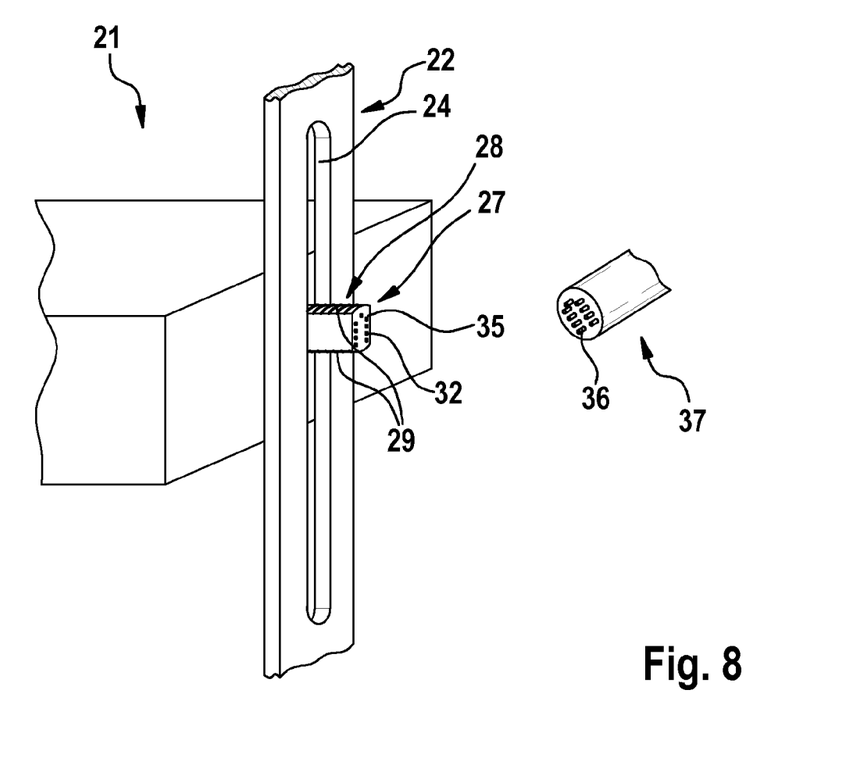
FIG. 8 shows a partial view of a medical appliance, a fastening plate, and a plug of a connection line according to the second illustrative embodiment.

FIG. 8 shows schematically that portion 28 of a support bolt 27 directed away from the appliance, which portion 28 is guided through the oblong hole 24 of a fastening plate 22. If a nut (not shown in FIG. 8) is fitted onto the outer thread 29 and tightened, the medical appliance 21 can in this way be held mechanically on the fastening plate 22. The end face 35 directed away from the appliance has a plurality of contact sockets 32, into which corresponding contact pins 36 of a plug 37 can be inserted. The support bolt 27 thus not only serves to mechanically hold the appliance 21, but also to connect it to an electrical connection line by plugging the plug 37 of the connection line onto that end of the support bolt 27 directed away from the appliance.

Figure 9:
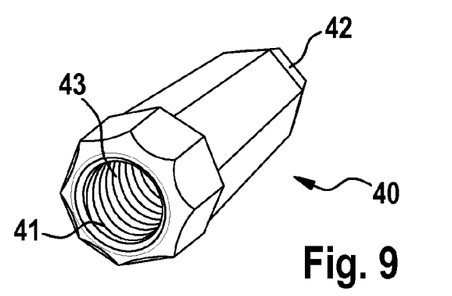
FIG. 9 shows a nut for screwing onto a support bolt according to an illustrative embodiment of the invention.

FIG. 9 shows a nut 40 designed as a union nut, which serves for mechanically fixing the medical appliance on the fastening plate 2, 22 (see FIGS. 1 to 8) and also for securing on the support bolt 7, 27 an electrical plug 37 that can be fitted onto the support bolt 7, 27. In a front area, the nut 40 has an inner thread 41, with which it can be screwed onto an outer thread 29 of a portion 28 of the support bolt 7, 27 directed away from the appliance (see FIGS. 6 and 8). In its rear area, the nut 40 has a tapering 42, by which the through-bore 43 of the nut 40 is tapered in such a way that a plug of a connection line is held inside the through-bore 43. For screwing it onto the support bolt 7, 27, the nut 40 is provided on its outside with flat surfaces, for example in the form of an octagon. The nut 40 can be designed in such a way that a special tool is needed for tightening it and loosening it. It is thus possible to prevent unauthorized release of the nut 40 and unauthorized removal of the appliance. However, the nut 40 can also be designed in such a way that it can be tightened and then released again without a tool. This permits particularly simple fitting of the appliance on the support device.

Figure 10:
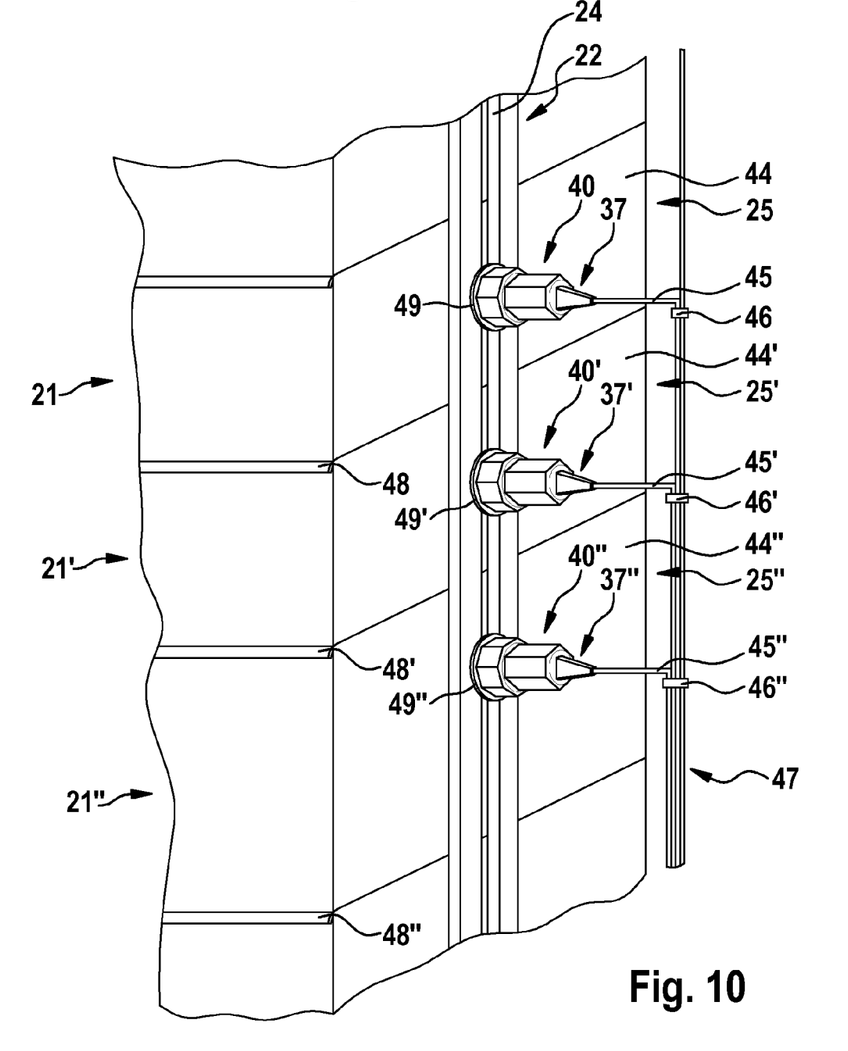
FIG. 10 shows a medical appliance system according to the second illustrative embodiment.

As is shown in FIG. 10, provision is made, according to an illustrative embodiment of the invention, that a plurality of medical appliances 21, 21', 21" can be stacked on top of one another. A support bolt protrudes in each case from a side wall 44, 44', 44" of the housing 25, 25', 25" of the appliance 21, 21', 21", is guided through the vertically extending oblong hole 24 of a fastening plate 22, and can be secured on the fastening plate 22 by the nut 40, 40', 40" designed as a union nut. To improve the bearing of the nut 40, 40', 40" on the fastening plate 22, a washer 49, 49', 49" is in each case arranged between the nut 40, 40', 40" and the fastening plate 22. At its end directed away from the respective appliance 21, 21', 21", the nut 40, 40', 40" is tapered in such a way that, when it is screwed onto the support bolt, the plug 37, 37', 37" of the connection line 45, 45', 45" routed to the respective appliance 21, 21', 21" is held on the support bolt. In this way, by mechanically fixing the appliance 21, 21', 21" on the fastening plate 22, an electrical connection can also be produced and secured against release without any further working steps. The connection lines 45, 45', 45" can be held together by cable binders 46, 46', 46", for example, and can belong to a cable tree 47 of an operating theater control system. The connection lines 45, 45', 45" comprise, for example, 5 volt, 12 volt or 24 volt supply lines, and also bus, video and/or audio signal lines and further data lines for operating the appliances 21, 21', 21" with the aid of a central control or computing unit.

Preferably, the bottom face of an appliance 21, 21' can in each case be placed with a form fit onto the top face of the appliance 21', 21" arranged underneath. On a lower edge of a front face of the housing of the appliance 21, 21', 21", a lip 48, 48', 48" is in each case arranged in such a way that the lip 48, 48', 48" protrudes forward relative to the upper edge of the front face of the housing of the respective appliance underneath and overlaps it, dimensionally flush, in the manner of a roof tile. In this way, entry of liquids that could splash onto the front face of the appliances during use of the appliances, for example in a surgical operation, and that could get in between the appliances in question, can be largely avoided even without a surrounding housing. As is indicated in FIG. 10, more than three appliances of the type described can be stacked.

For the sake of clarity, not all reference signs are shown in all of the figures. Reference signs that are not explained in connection with one figure have the same meaning as in the other figures.

The invention claimed is:

1. A medical appliance for use in a medical environment, comprising:
    a housing;
    a support structure;
    at least one support bolt configured to hold the support structure on a support device;
    at least one electrical line extending internally through the at least one support bolt; and
    an attachment mechanism positioned relative to the at least one support bolt and electrically connected to the at least one electrical line, the attachment mechanism configured to electrically connect the at least one electrical line to at least one external electrical connection line of the medical environment;
    wherein the attachment mechanism carries a plurality of electrical contacts;
    wherein the plurality of electrical contacts include contact pins oriented in an axial direction of the at least one support bolt;
    wherein the contact pins are configured to be fittingly connected to corresponding sockets of a plug of the at least one external electrical connection line; and
    wherein the at least one electrical line is connected to the contacts pins and extends internally through the at least one support bolt to at least one corresponding contact inside the housing.

2. The medical appliance of claim 1, wherein the at least one support bolt is a single support bolt.

3. The medical appliance of claim 1, wherein the attachment mechanism is arranged on an end face of the at least one support bolt.

4. The medical appliance of claim 1, wherein at least a portion of the at least one support bolt is threaded.

5. The medical appliance of claim 2, wherein the single support bolt has two first flat outer surfaces lying opposite each other with respect to a longitudinal axis of the single support bolt.

6. The medical appliance of claim 5, wherein the single support bolt has two second flat outer surfaces lying opposite each other with respect to the longitudinal axis of the single support bolt.

7. The medical appliance of claim 6, wherein the two first flat outer surfaces and the two second flat outer surfaces are mutually offset by approximately 90° with respect to the longitudinal axis of the single support bolt.

8. The medical appliance of claim 1,
    wherein at least a portion of the housing forms the support structure; and
    wherein the at least one support bolt is screwed or welded onto a wall of the housing.

9. A medical appliance system, comprising:
    a first medical appliance having a first support bolt, a first electrical line extending internally through the first support bolt, and a first attachment mechanism positioned relative to the first support bolt and electrically connected to the first electrical line, the first attachment mechanism configured to electrically connect the first electrical line to a first external electrical connection line;
    a support device having a fastening plate with a first aperture,
    the first support bolt of the first medical appliance configured to be received within the first aperture of the fastening plate to hold the first medical appliance on the support device; and
    a nut configured to be screwed onto an area of the first support bolt that is configured to be guided through the first aperture, wherein said nut is configured to be used to positionally fix the first medical appliance on the fastening plate.

10. The medical appliance system of claim 9, wherein the first aperture of the fastening plate is a hole in a grid-like pattern of holes.

11. The medical appliance system of claim 9, further comprising:
    a second medical appliance having a second support bolt, a second electrical line extending internally through the second support bolt, and a second attachment mechanism positioned relative to the second support bolt and electrically connected to the second electrical line, the second attachment mechanism configured to electrically connect the second electrical line to the first external electrical connection line or a second external electrical connection line; and
    wherein the second support bolt of the second medical appliance is configured to be received within the first aperture or a second aperture of the fastening plate to hold the second medical appliance on the support device.

12. The medical appliance system of claim 11, wherein the first medical appliance includes a housing with a bottom face and the second medical appliance includes a housing with a top face, wherein the bottom face and the top face are configured such that the bottom face of the first medical appliance can be placed with a form fit onto the top face of the second medical appliance.

13. The medical appliance system of claim 12, wherein the respective housings of the first and second medical appliances each are substantially fully closed with a front wall; and
    wherein at least the first medical appliance carries, on a lower edge of the front wall, a lip which, when the first medical appliance is placed onto the second medical appliance, overlaps an upper edge of the front wall of the second medical appliance.

14. The medical appliance system of claim 13, wherein the respective housings of the first and second medical appliances each have a rear wall, a side wall, or a combination of a rear wall and side wall; and
    wherein the respective first and second support bolts of the first and second medical appliances each protrude from the respective rear wall or side wall.

15. The medical appliance system of claim 9, wherein the first medical appliance includes a housing, and the first support bolt is screwed or welded onto a wall of the housing.

16. The medical appliance system of claim 9, wherein the first aperture of the fastening plate is an oblong hole.

\* \* \* \* \*